United States Patent [19]

Bondinell et al.

[11] 4,218,464

[45] Aug. 19, 1980

[54] 4- AND 5-SUBSTITUTED 2,3-DIHYDRO-1H-ISOINDOLES, PHARMACEUTICAL COMPOSITIONS AND METHOD OF INHIBITING PHENYLETHANOLAMINE N-METHYLTRANSFERASE

[75] Inventors: William E. Bondinell, Cherry Hill, N.J.; Robert G. Pendleton, Philadelphia, Pa.

[73] Assignee: SmithKline Corporation, Philadelphia, Pa.

[21] Appl. No.: 17,005

[22] Filed: Mar. 2, 1979

[51] Int. Cl.$^2$ .................... A61K 31/40; C07D 209/44
[52] U.S. Cl. ................................. 424/274; 260/326.1
[58] Field of Search ..................... 260/326.1; 424/274

[56] References Cited

PUBLICATIONS

C. Grogan, J. Med. Chem. 10(4), pp. 621–623 (1967), omega-Azabicyclic Butyrophenones.
W. Rosen et al., JACS 79, pp. 3167–3174, (1957), Tetrachloroisoindolines and Related Systems.
W. Adcock et al., Chem. Abst. 84: 179060d (1976).
R. Kreher et al., Chem. Abst. 82: 57506s (1975).
J. Bornstein et al., Chem. Abst. 82: 139890b (1975).

*Primary Examiner*—Nicholas S. Rizzo
*Assistant Examiner*—M. C. Eakin
*Attorney, Agent, or Firm*—Joseph A. Marlino; Richard D. Foggio; William H. Edgerton

[57] ABSTRACT

Pharmaceutical compositions and methods of inhibiting phenylethanolamine N-methyltransferase using novel 2,3-dihydro-1H-isoindole compounds having 4- and 5-substituents.

10 Claims, No Drawings

4- AND 5-SUBSTITUTED 2,3-DIHYDRO-1H-ISOINDOLES, PHARMACEUTICAL COMPOSITIONS AND METHOD OF INHIBITING PHENYLETHANOLAMINE N-METHYLTRANSFERASE

This invention relates to new pharmaceutical compositions and methods of inhibiting phenylethanolamine N-methyltransferase with 2,3-dihydro-1H-isoindole compounds having 4- and 5-substituents.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The 2,3-dihydro-1H-isoindole compounds of the pharmaceutical compositions and methods of this invention inhibit phenylethanolamine N-methyltransferase and thus reduce the formation of epinephrine. They are therefore useful in situations where there is overproduction of epinephrine or where epinephrine production is detrimental.

The compounds which are the active ingredients of the pharmaceutical compositions and methods of this invention are represented by the following formula:

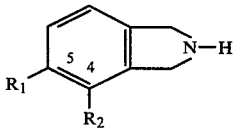

FORMULA 1 in which:

$R_1$ and and $R_2$ are chloro, bromo, fluoro, iodo or trifluoromethyl, $R_1$ and $R_2$ being the same or different and in the 4- and 5-positions and pharmaceutically acceptable acid addition salts thereof.

The 5-chloro substituted compounds of this invention are prepared by the following procedure:

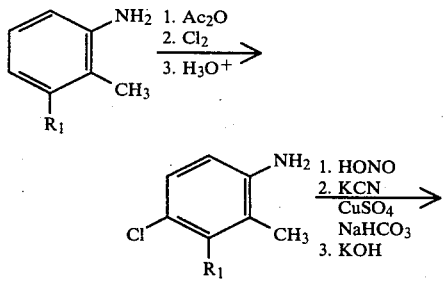

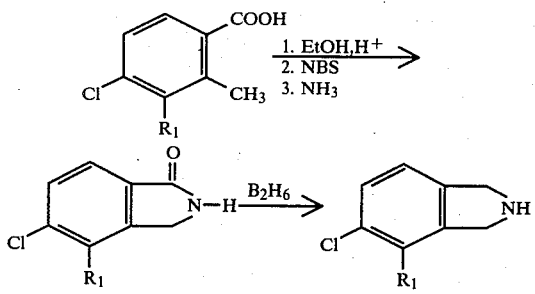

The term $R_1$ is defined as above.

According to the above procedure, the substituted 2,3-dihydro-1H-isoindoles are prepared by reacting a 3-substituted-2-methylaniline with acetic anhydride and then with chlorine in acetic acid followed by hydrolysis to form the corresponding 3,4-disubstituted methylaniline. The 3,4-disubstituted-2-methylaniline is diazotized and converted, via the nitrile, to the 3,4-disubstituted-2-methylbenzoic acid. The acid is esterified, treated with N-bromosuccinimide and then with ammonia to give the 4,5-disubstituted-2,3-dihydro-1H-indol-1-one which is reduced to the desired 4,5-disubstituted-2,3-dihydro-1H-isoindole.

In an alternative procedure, the 4,5-disubstituted 2,3-dihydro-1H-isoindoles are prepared by reacting a 2,3- or 3,4-disubstituted aniline with chloral hydrate, hydroxylamine hydrochloride, sodium sulfate, and hydrochloric acid and then with concentrated sulfuric acid to yield the corresponding 6,7- or 4,5-disubstituted isatin. The isatin is treated with m-chloroperbenzoic acid and then with sodium methoxide to yield the properly substituted methyl anthranilate.

The anthranilate is converted to the ortho-cyano-benzoate which is hydrolyzed to the 3,4-disubstituted phthalic acid. The acid is reduced with diborane to the corresponding diol. The diol is then converted to the 3,4-disubstituted-1,2-bis(bromomethyl)benzene which is cyclized with the sodium salt of toluenesulfonamide and hydrolyzed to give the 4,5-disubstituted-2,3-dihydro-1H-isoindoles.

Pharmaceutically acceptable acid addition salts of the compounds of Formula 1 are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

2,3-Dihydro-1H-isoindole and halo substituted 2,3-dihydro-1H-isoindoles are generally known in the art. The latter compounds are disclosed in *J. Med. Chem.* 10(4):621-3, 1967 as tranquilizers.

The basic activity of the compounds of this invention is demonstrated by inhibition of phenylethanolamine N-methyltransferase *in vitro* by the assay procedure described by Pendleton and Snow, *Molecular Pharmacology*, 9, 718–725, 1973, at various compound concentrations. For example, at a concentration of $1.0 \times 10^{-4}$ M, a preferred compound of this invention 4,5-dichloro-2,3-dihydro-1H-isoindole inhibits phenylethanolamine N-methyltransferase by 98%.

The pharmaceutical compositions of this invention to inhibit phenylethanolamine N-methyltransferase comprise a pharmaceutical carrier and, as the active ingredient, a 2,3-dihydro-1H-isoindole compound of Formula 1. The active ingredient will be present in the compositions of this invention in an effective amount to inhibit phenylethanolamine N-methyltransferase.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a 2,3-dihydro-1H-isoindole compound of Formula 1.

Preferably the compounds of Formula 1 are administered in conventional dosage unit forms prepared by combining an appropriate dose of the compound with standard pharmaceutical carriers.

Preferably the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

141 g. of 3-chloro-2-methylaniline (1 mol.) was added to a stirred mixture of 200 ml. of acetic acid and 102 g. (1 mol.) of acetic anhydride and heated to 95° C. for approximately one hour. The mixture was poured into water and filtered to give 3-chloro-2-methylacetanilide.

The above acetanilide, 139 g. (10.76 mol.) was suspended in 300 ml. of acetic acid and treated with a solution of chlorine, 54 g. (0.76 mol.) in 1.1 L. of acetic acid over a 20 minute period. The mixture was filtered, the filter cake slurred in water and again filtered to yield 3,4-dichloro-2-methylacetanilide.

The dichloroacetanilide 80 g. (0.37 mol.) was dissolved in 112 g. of concentrated sulfuric acid and 160 ml. of water and refluxed. The resulting solution was treated with 200 ml. of acetic acid, cooled to 5° C. and diazotized with 31 g. (0.44 mol.) of sodium nitrite in 60 ml. of water.

Potassium cyanide 130 g. (2 mol.) was added to a solution of cupic sulfate pentahydrate 120 g. (0.48 mol.) in 600 ml. of water maintained below 20° C. Sodium bicarbonate (268 g.) and 300 ml. of benzene were added, the mixture warmed to 50° C. and the solution of diazonium salt was added carefully in portions, below the surface, over a 30 minute period. The mixture was stirred and then extracted with benzene. The residue was distilled and recrystallized from methanol to yield 3,4-dichloro-2-methyl-benzonitrile, m.p. 78°–79° C.

The above prepared benzonitrile 15 g. (0.08 mol.) was dissolved in 150 ml. of 10% aqueous sodium hydroxide in 150 ml. of ethanol and refluxed, cooled, acidified with concentrated hydrochloric acid, filtered, washed with water and dried to yield 3,4-dichloro-2-methylbenzoic acid.

12.0 g. (0.058 mol.) of dichloro-3-methylbenzoic acid and 75 ml. of ethyl orthoformate in 100 ml. of ethanol was saturated with hydrogen chloride and refluxed to give ethyl 3,4-dichloro-2-methylbenzoate.

A mixture of the above benzoate 22.5 g. (0.096 mol.) and 17.2 g. (0.096 mol.) of N-bromosuccinimide in 1 L. of carbon tetrachloride was heated to reflux, irradiated with a sunlamp and treated with 3 g. of dibenzoylperoxide in small portions until the reaction was complete. The mixture was filtered, washed with water, dried and evaporated to give ethyl-2-bromomethyl-3,4-dichlorobenzoate.

Ammonia was bubbled through a solution of ethyl 2-bromomethyl-3,4-dichlorobenzoate (25 g, 0.08 mol.) in 250 ml. of dimethylformamide for ½ hour at 0° C. The mixture was stirred for one hour at 25° C., poured on crushed ice and filtered. The solid was chromatographed on silica gel eluted ether, ethyl acetate and then acetone to give 4,5-di-chloro-2,3-dihydro-1H-isoindol-1-one.

8.1 g. (0.04 mol.) of the above isoindolone in 250 ml. of tetrahydrofuran was treated with 100 ml. of 1.0 M diborane in tetrahydrofuran and refluxed. Excess diborane was destroyed with methanol and the solvent was evaporated. The residual oil was dissolved in ethyl acetate and 3 N hydrochloric acid and the mixture evaporated and partitioned between ethyl acetate and aqueous sodium bicarbonate. The ethyl acetate layer was treated with ethereal hydrogen chloride filtered and the filter cake recrystallized twice from isopropanol-ethyl acetate to give 4,5-dichloro-2,3-dihydro-1H-isoindole hydrochloride, m.p. 240°–241° C.

EXAMPLE 2

Following the procedure of Example 1, the following substituted aniline compounds:
3-bromo-2-methylaniline
3-fluoro-2-methylaniline 3-iodo-2-methylaniline
3-trifluoromethyl-2-methylaniline
are used as starting materials to give the following products respectively:

5-chloro-4-bromo-2,3-dihydro-1H-isoindole
5-chloro-4-fluoro-2,3-dihydro-1H-isoindole
5-chloro-4-iodo-2,3-dihydro-1H-isoindole
5-chloro-4-trifluoromethyl-2,3-dihydro-1H-isoindole

EXAMPLE 3

3,4-Bis(trifluoromethyl)aniline (115 g., 0.5 mol.) in 43 ml. of concentrated hydrochloric acid and 300 ml. of water is mixed with chloral hydrate (90 g., 0.54 mol.) in 1.2 L. of water, sodium sulfate (571 g.) in 725 ml. of water and hydroxylamine hydrochloride (104 g., 1.5 mol.) in 500 ml. of water, heated to reflux, cooled and filtered to give 3,4-bis(trifluoromethyl)isonitrosoacetanilide.

The isonitrosoacetanilide (465 g., 1.55 mol.) is added gradually to 1.5 L. of concentrated sulfuric acid stirred at 90° C. The mixture is stirred for 30 minutes, cooled, poured onto crushed ice and filtered. Fractional crystallization of the filter cake from ethanol gave 4,5-bis(trifluoromethyl)isatin.

4,5-Bis(trifluoromethyl)isatin (283 g., 1 mol.) is suspended in 1 L. of ethyl acetate and treated with m-chloroperbenzoic acid (172 g., 1 mol.), stirred until the oxidation is complete to yield 5,6-bis(trifluoromethyl)-isatoic anhydride.

The anhydride (195 g., 0.65 mol.) is suspended in 750 ml. of dry methanol and treated with sodium methoxide. The mixture is refluxed for 30 minutes until evolution of carbon dioxide stopped. The mixture is cooled, filtered, acidified with acetic acid and evaporated to yield methyl 5,6-bis(trifluoromethyl)anthranilate.

Methyl 5,6-bis(trifluoromethyl)anthranilate (28.5 g., 0.1 mol.) was diazotized and converted to the nitrile following the procedure of Example 1 to give methyl 2,3-bis(trifluoromethyl)-6-cyanobenzoate. The cyanobenzoate (38.5 g., 0.13 mol.) was heated to reflux with 100 ml. of concentrated hydrochloric acid for sixteen hours. The mixture was cooled and extracted with ether to give 3,4-bis-(trifluoromethyl)phthalic acid.

3,4-Bis(trifluoromethyl)phtalic acid (33 g., 0.11 mol.) in 70 ml. of tetrahydrofuran is refluxed with 450 ml. of 1.0 M diborane in tetrahydrofuran for four hours. Excess diborane is destroyed with water to yield 3,4-bis(-trifluoro- methyl)-1,2-benzenedimethanol.

3,4-Bis(trifluoromethyl)-1,2-benzenedimethanol (20.0 g., 0.07 mol.) was dissolved in 300 ml. of hot concentrated hydrobromic acid, and stirred at 50° C. for four hours. The mixture was extracted with ether and the residue obtained after evaporating the ether is purified by chromotography on silica gel eluted with carbon tetrachloride to give 1,2-bis(bromomethyl)-3,4-bis(trifluoromethyl)benzene.

1,2-Bis(bromomethyl)-3,4-bis(trifluoromethyl)benzene (120 g., 0.3 mol.) in 450 ml. of ethanol is refluxed and treated with a solution of the sodium salt of p-methyl-benzene sulfonamide prepared by dissolving sodium (15.2 g., 0.66 mol.) in a mixture of p-methylbenzenesulfonamide (51.2 g., 0.3 mol.) in 650 ml. of methanol. The mixture is refluxed for two hours, cooled, neutralized with acetic acid and filtered to give 4,5-bis(trifluoromethyl)-2,3-di-hydro-1H-isoindole.

4,5-Bis(trifluoromethyl)-N-(p-tolylsulfonyl)-N-(p-tolylsulfonyl)-2,3-dihydro-1H-isoindole (24.0 g., 0.058 mol.) and phenol (20 g.) in 200 ml. of concentrated hydrobromic acid and 100 ml. of propionic acid is refluxed for two hours, cooled, washed with ether and made alkaline. The alkaline mixture is extracted with methylene chloride to give 4,5-bis(trifluoromethyl)-2,3-dihydro-1H-isoindole.

EXAMPLE 4

Following the procedure of Example 3 the following substituted anilines:

3,4-dibromoaniline
3,4-difluoroaniline
3-chloro-4-bromoaniline are used as starting materials to give the following products respectively.

4,5-dibromo-2,3-dihydro-1H-isoindole
4,5-difluoro-2,3-dihydro-1H-isoindole
4-chloro-5-bromo-2,3-dihydro-1H-isoindole

EXAMPLE 5

| Ingredients | Mg. Capsule |
|---|---|
| 4,5-dichloro-2,3-dihydro-1H-isoindole | 150 |
| Lactose | 150 |

The above ingredients are mixed and filled into a hard gelatin capsule.

EXAMPLE 6

| Ingredients | Mg. Tablet |
|---|---|
| 4,5-bis(trifluoromethyl)-2,3-dihydro-1H-isoindole | 50 |
| Calcium Sulfate Dihydrate | 150 |
| Sucrose | 25 |
| Starch | 15 |
| Talc | 5 |
| Stearic acid | 3 |

The sucrose, calcium sulfate and 2,3-dihydro-1H-isoindole are thoroughly mixed and granulated with hot 10% gelatin solution. The wetted mass is passed through a No. 6 mesh screen directly onto drying trays. The granules are dried at 120° C. and passed through a No. 20 mesh screen, mixed with starch, talc and stearic acid and compressed into tablets.

Two tablets are administered three times a day.

What is claimed is:

1. A compound of the formula:

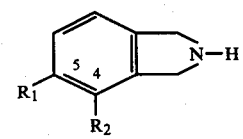

in which
R$_1$ and R$_2$ are chloro, bromo, fluoro, iodo or trifluoromethyl, R$_1$ and R$_2$ being the same or different and in the 4- and 5-position or a pharmaceutically acceptable acid addition salt thereof.

2. The compound of claim 1 in which R$_1$ and R$_2$ are chloro.

3. The compound of claim 1 in which R$_1$ is chloro and R$_2$ is trifluoromethyl.

4. The compound of claim 1 in which R$_1$ and R$_2$ are trifluoromethyl.

5. A pharmaceutical composition in dosage unit form for inhibiting phenylethanolamine N-methyltransferase comprising a pharmaceutical carrier and an effective amount of a chemical compound as defined in claim 1.

6. A pharmaceutical composition in dosage unit form for inhibiting phenylethanolamine N-methyltransferase comprising a pharmaceutical carrier and an effective amount of a chemical compound as defined in claim 2.

7. The pharmaceutical composition of claim 5 in which the compound is present in an amount of from about 50 mg. to about 1000 mg.

8. The pharmaceutical composition of claim 5 wherein the composition is in the form of a tablet or capsule.

9. A method of inhibiting phenylethanolamine N-methyltransferase which comprises administering to an animal requiring said treatment an amount sufficient to produce said inhibition of a chemical compound as defined in claim 1.

10. The method of claim 9 in which the compound is administered in a daily dose of from about 100 mg. to about 2000 mg.

* * * * *